US008559010B2

(12) United States Patent
Gross et al.

(10) Patent No.: US 8,559,010 B2
(45) Date of Patent: Oct. 15, 2013

(54) STRUCTURAL ASSEMBLY AND METHODS FOR FACILITATING CORROSION INSPECTION

(75) Inventors: Gwen M. Gross, Redmond, WA (US); Christopher L. Broadbent, Kent, WA (US)

(73) Assignee: The Boeing Company, Chicago, IL (US)

( * ) Notice: Subject to any disclaimer, the term of this patent is extended or adjusted under 35 U.S.C. 154(b) by 391 days.

(21) Appl. No.: 12/643,728

(22) Filed: Dec. 21, 2009

(65) Prior Publication Data

US 2011/0149283 A1 Jun. 23, 2011

(51) Int. Cl.
*G01J 3/46* (2006.01)
(52) U.S. Cl.
USPC .......................................................... 356/402
(58) Field of Classification Search
USPC ..................................... 356/402, 417; 385/12
See application file for complete search history.

(56) References Cited

U.S. PATENT DOCUMENTS

| | | | | |
|---|---|---|---|---|
| 5,646,400 A | * | 7/1997 | Perez et al. | 250/227.18 |
| 2003/0231301 A1 | | 12/2003 | Floyd et al. | |
| 2005/0044943 A1 | * | 3/2005 | Godeau et al. | 356/432 |
| 2005/0082467 A1 | * | 4/2005 | Mossman | 250/227.16 |
| 2005/0135546 A1 | | 6/2005 | Ponstingl et al. | |
| 2008/0150555 A1 | * | 6/2008 | Wang et al. | 324/693 |
| 2008/0312847 A1 | | 12/2008 | Safai et al. | |

OTHER PUBLICATIONS

Amatore, C. et al., *Remote Fluorescence Imaging of Dynamic Concentration Profile With Micrometer Resolution Using a Coherent Optical Fiber Bundle*, Analytical Chemistry, vol. 76, No. 24, Dec. 2004, pp. 7202-7210.
Kendig, M., *Past, Present and Future 'Smart' Protective Coatings*, Rockwell Scientific Company LLC, undated, pp. 1-10.
Liu, G. et al., *Use of a Fluorescent Indicator in Monitoring Underlying Corrosion on Coated Aluminum 2024-T4*, Journal of the Electrochemical Society, 156 (4), 2009, pp. C160-C166.
Panova, A. A. et al., *In Situ Fluorescence Imaging of Localized Corrosion With a pH-Sensitive Imaging Fiber*, Analytical Chemistry, vol. 69, No. 8, Apr. 1997, 1635-1641.
Zhang, J. et al., *Painted as a Corrosion Sensor; Acrylic Coating Systems*, Mat. Res. Soc. Symp. Proc. vol. 503, Materials Research Society, 1998, pp. 15-24.

(Continued)

*Primary Examiner* — Kara E Geisel
(74) *Attorney, Agent, or Firm* — Alston & Bird LLP (57) ABSTRACT

A structural assembly and methods are provided to facilitate corrosion inspection, such as in those regions of a structure that may otherwise be visibly inspected only following at least partial disassembly of the structure. The structural assembly may include a structure and a coating disposed upon at least a portion of the structure that has optical properties that change in response to corrosion. The structural assembly may also include a fiber optic sensing network including a plurality of optical fibers and a sensor. The plurality of optical fibers are configured to expose the coating to incident optical signals and to receive responsive optical signals at least partially dependent upon any change in the optical properties of the coating. The sensor is configured to receive the responsive optical signals from the plurality of optical fibers. This sensor may also be configured to analyze the responsive optical signals to detect corrosion.

20 Claims, 4 Drawing Sheets

(56) References Cited

OTHER PUBLICATIONS

Creech, G. et al., *NASA Evaluates Fiber Optic Technology for Future Aircraft Efficiency*, News Releases, Jul. 14, 2008, pp. 1-2.
*Painted Changes Color to Reveal Corrosion on Aircraft* [online] [retrieved Dec. 21, 2009]. Retrieved from the Internet: <URL: http://www.sciencedaily.com/releases/1998/03/980330073403.htm>. 2 pages.
*Painted Changes Color to Reveal Corrosion on Aircraft*, [online] [retrieved Dec. 21, 2009]. Retrieved from the Internet: <URL: http://researchnews.osu.edu/archive/pnkpaint.htm>. 2 pages.
Delaney, K. et al., *Battelle Creates Smart Coating to Fight Rust: Innovation by Scientists Can Lead to Billions in Savings for National Defense, Airlines*, Nanotechnology Now, posted Jan. 22, 2009, 4 pages.
Search Report and Written Opinion for International Application No. PCT/US2010/057165, mailed Feb. 7, 2011; 10 pages.

\* cited by examiner

STRUCTURAL ASSEMBLY AND METHODS FOR FACILITATING CORROSION INSPECTION

TECHNOLOGICAL FIELD

Embodiments of the present invention relate generally to the inspection of a portion of a structure and, more particularly, to the inspection of at least a portion of a structure in order to detect corrosion.

BACKGROUND

Once in service, many, if not most, structures experience corrosion in response to their exposure to the elements, such as rain, humidity, elevated temperatures, salt and other chemicals, and the like. For example, many buildings and vehicles, such as ships and automobiles, may experience corrosion following exposure to the elements over time.

As corrosion may cause the integrity of the structure to degrade, it may be desirable in at least some application to prevent or at least reduce the rate of corrosion. As such, coatings have been developed that at least partially inhibit corrosion. For example, coatings that include chrome may reduce the rate at which the underlying structure corrodes. However, the corrosion inhibiting coating may disadvantageously increase the cost of the resulting structure and/or may introduce other disadvantages. For example, at least some corrosion inhibiting coatings may be potentially harmful to the environment such that special precautions are taken, both while coating the structure and then when disposing of the coated structure, thereby disadvantageously increasing the costs associated with the structure. Additionally, corrosion inhibiting coatings may be exhausted over time, thereby reducing the inhibition to corrosion provided by the coating. For example, a coating that includes chrome may change over time with the chrome leaching from the coating so as to reduce the corrosion inhibition otherwise provided by the coating.

In addition to or instead of efforts to inhibit the corrosion of various structures, the structures may be inspected, such as on a periodic or other scheduled basis, in order to detect corrosion and, if detected, to remediate the deleterious effects of the corrosion. While the visible regions of a structure may be inspected relatively easily such that inspections may be conducted with regularity, at least those regions of a structure that are hidden from view, such as those regions of a structure that require disassembly of at least a portion of the structure in order to access and to inspect the region may only be inspected occasionally because of the time and expense associated with the inspection process. Moreover, the disassembly associated with the inspection of otherwise inaccessible regions of the structure may, in some instances, damage the structure or otherwise cause portions of the structure to need to be replaced, thereby further increasing the time and expense associated with such an inspection.

Figure 1:
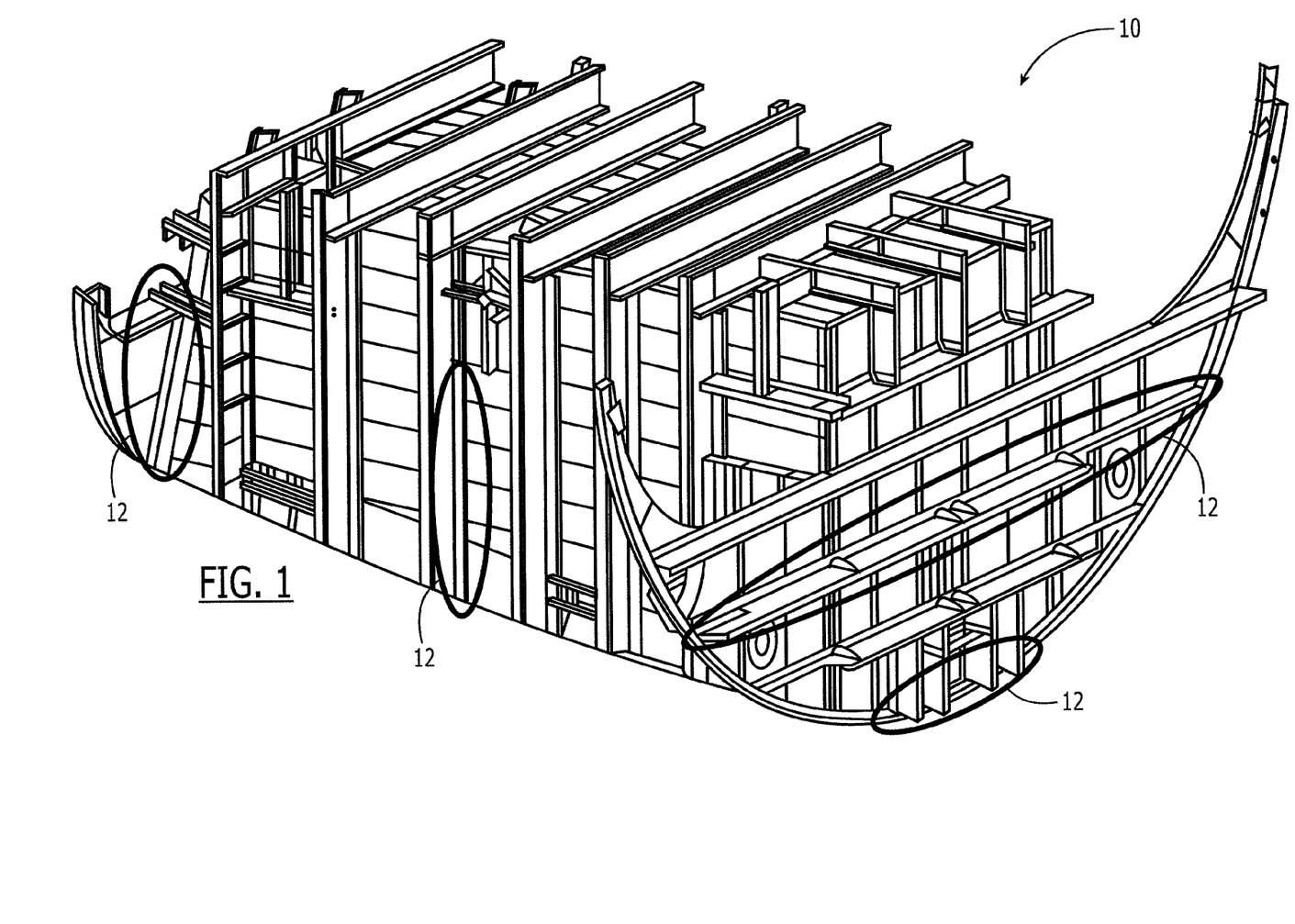
FIG. 1 is a fragmentary perspective view of a portion of an interior structural region of an aircraft with at least portions of the interior structural region being incapable of visual inspection without at least partial disassembly of the structure.

By way of example, FIG. 1 depicts an interior region 10 of an aircraft. Although it may be desirable to detect corrosion of the illustrated interior region of the aircraft, at least a portion of the interior region, such as the circled regions 12, may be hidden from view and may therefore require at least partial disassembly of the interior region of the aircraft in order to conduct a complete inspection.

To facilitate the inspection of regions of a structure that are not visible without requiring disassembly of a portion of the structure, inspection techniques utilizing ultrasonic signals or electromagnetic currents or signals have been developed. While these inspection techniques may be useful in at least some circumstances, these inspection techniques may be limited in their application due to, for example, the underlying materials from which the structure is fabricated, the configuration of the structure and the like.

The foregoing inspection techniques, such as the disassembly of a portion of the structure in order to visually inspect the structure or the inspection of a structure utilizing ultrasonic or electromagnetic inspection techniques, generally require the structure to be taken out service for some period of time. As a result, such inspections are generally only performed periodically or in accordance with a predefined schedule. For example, some structures that are inspected by disassembling a portion of the structure in order to visibly inspect that portion of the structure may only be fully inspected every few years, such as every five or six years. Thus, the effects of corrosion on that portion of the structure during the period of time between inspections may cause degradation of the structure and may require more extensive repairs or rework of the structure than if the structure had been inspected more frequently and the corrosion detected closer to its onset.

As such, it would be desirable to provide improved techniques for detecting corrosion including, for example, corrosion that may occur in regions of a structure that are only visible following the partial disassembly of the structure.

BRIEF SUMMARY OF THE INVENTION

A structural assembly and methods are therefore provided according to embodiments of the present invention in order to facilitate corrosion inspection. In this regard, the structural assembly and methods of one embodiment facilitate corrosion inspection in those regions of a structure that may otherwise be visibly inspected only following at least partial disassembly of the structure. As such, the structural assembly and methods may permit corrosion inspections to be conducted in a more efficient and cost effective manner, thereby allowing the corrosion inspections to occur more regularly and reducing the damage that may be caused by corrosion during the period between inspections.

In one embodiment, a structural assembly is provided that includes a structure and a coating disposed upon at least a portion of the structure and having optical properties that are configured to change in response to corrosion. For example, the coating may be configured to change in color or to luminesce in response to corrosion. The structural assembly of this embodiment also includes a fiber optic sensing network including a plurality of optical fibers and a sensor. The plurality of optical fibers are configured to expose the coating to incident optical signals and to receive responsive optical signals at least partially dependent upon any change in the optical properties of the coating in response to corrosion. The sensor, in turn, is configured to receive the responsive optical signals from the plurality of optical fibers. This sensor may also be configured to analyze the responsive optical signals and to detect corrosion. In one embodiment, the structural assembly also includes a user interface configured to provide information regarding corrosion of the structure in response to analysis of the responsive optical signals by the sensor.

The plurality of optical fibers of one embodiment extend along at least a portion of the structure. Indeed, at least a portion of the structure inspected by the fiber optic sensing network of one embodiment may include a region that is incapable of visual inspection absent at least partial disassembly of the structure. For example, the portion of the structure inspected by the fiber optic sensing network may include an interior structure region of an aircraft.

In another embodiment, a method of constructing a corrosion inspection system is provided. The method of this embodiment coats at least a portion of a structure with a coating having optical properties that change in response to corrosion. For example, at least a portion of the structure may be coated with a coating that is configured to change in color or to luminesce in response to corrosion. The method of this embodiment also extends a plurality of optical fibers along at least the portion of the structure that is coated such that the optical fibers are in optical communication with the coating. In this regard, the optical fibers may be extended along a region of the structure that is incapable of visual inspection absent at least partial disassembly of the structure, such as within an interior structural region of an aircraft. Further, the method of this embodiment provides an optical source configured to provide incident optical signals to the plurality of optical fibers and a sensor configured to receive responsive optical signals from the plurality of optical fibers following interaction of the optical signals with the coating so as to permit the responsive optical signals to be analyzed to detect corrosion. The method may also provide a user interface configured to provide information regarding corrosion of the structure in response to analysis of the responsive optical signals by the sensor.

According to a further embodiment, a method of inspecting a structure for corrosion may be provided. The method includes exposing a coating disposed upon at least a portion of the structure to incident optical signals being delivered by at least one optical fiber. The coating is configured to have optical properties that change in response to corrosion. For example, the coating may be configured a change color or to luminesce in response to corrosion. A method of this embodiment may also receive responsive optical signals via at least one optical fiber in response to having exposed the coating to the incident optical signals with the responsive optical signals being at least partially dependent upon any change in the optical properties of the coating in response to corrosion. The method of this embodiment also includes analyzing the responsive optical signals to detect corrosion.

In one embodiment, the method also includes delivering the incident optical signals and returning the responsive optical signals via plurality of optical fibers extending along at least a portion of the structure. In this regard, exposing the coating may include exposing the coating disposed upon at least a portion of the structure that is incapable of visual inspection absent at least partial disassembly of the structure. For example, exposing the coating may include exposing the coating disposed upon an interior structure region of an aircraft. Regardless of the portion of the structure that is exposed to the incident optical signals, the coating may be exposed, the responsive optical signals may be received and the responsive optical signals may be analyzed on a repeating basis in accordance with a predefined schedule.

The analysis of the responsive optical signals to detect corrosion may include detecting responsive optical signals that result from having exposed the coating to incident optical signals following the change in the optical properties of the coating in response to corrosion. A method of this embodiment may also include providing information regarding corrosion of the structure in response to analysis of the responsive optical signals.

BRIEF DESCRIPTION OF THE SEVERAL VIEWS OF THE DRAWING(S)

Having thus described embodiments of the invention in general terms, reference will now be made to the accompanying drawings, which are not necessarily drawn to scale, and wherein:

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 2:
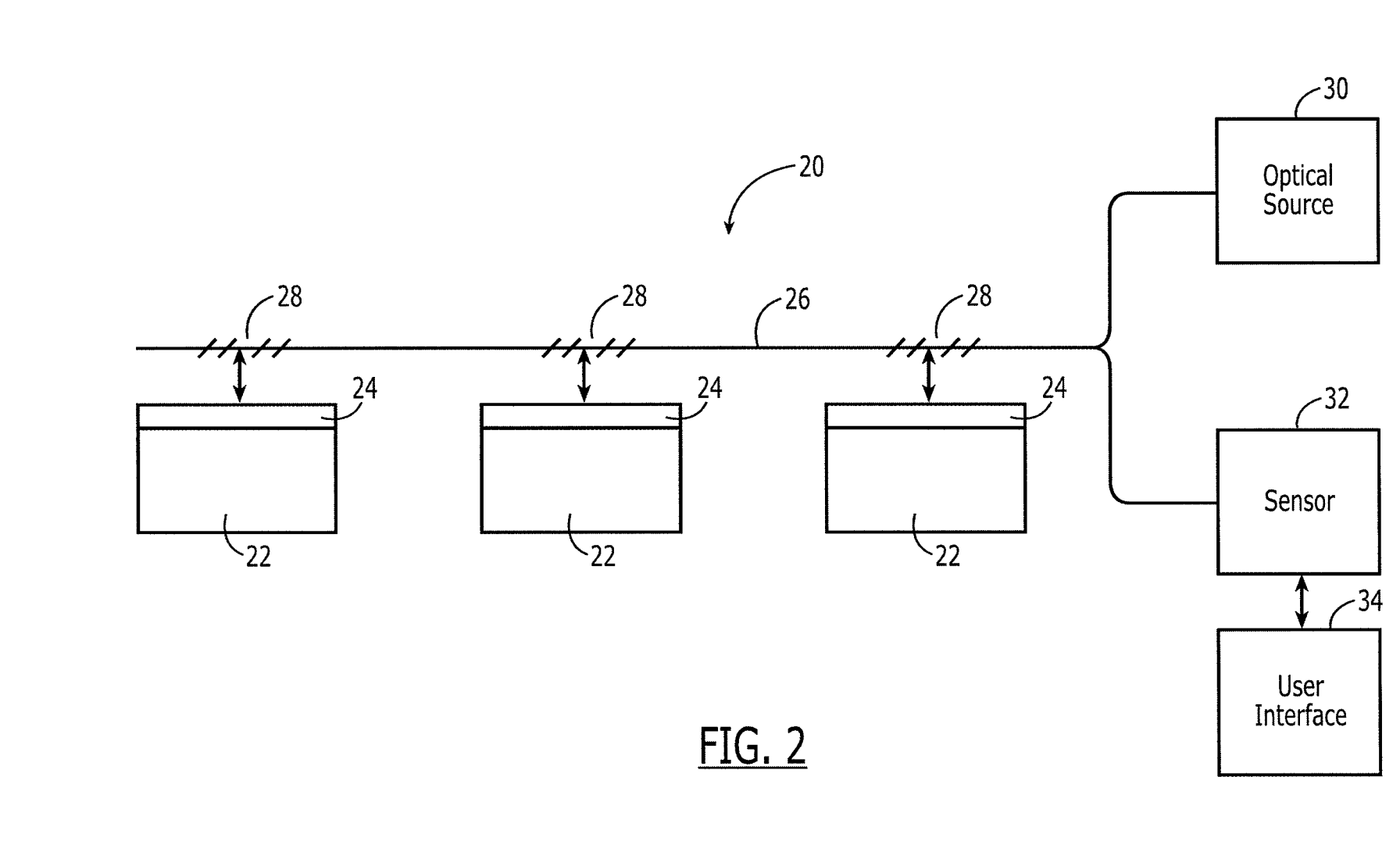
FIG. 2 is a schematic representation of a system configured to facilitate corrosion inspection in accordance with one embodiment of the present invention.
Figure 3:
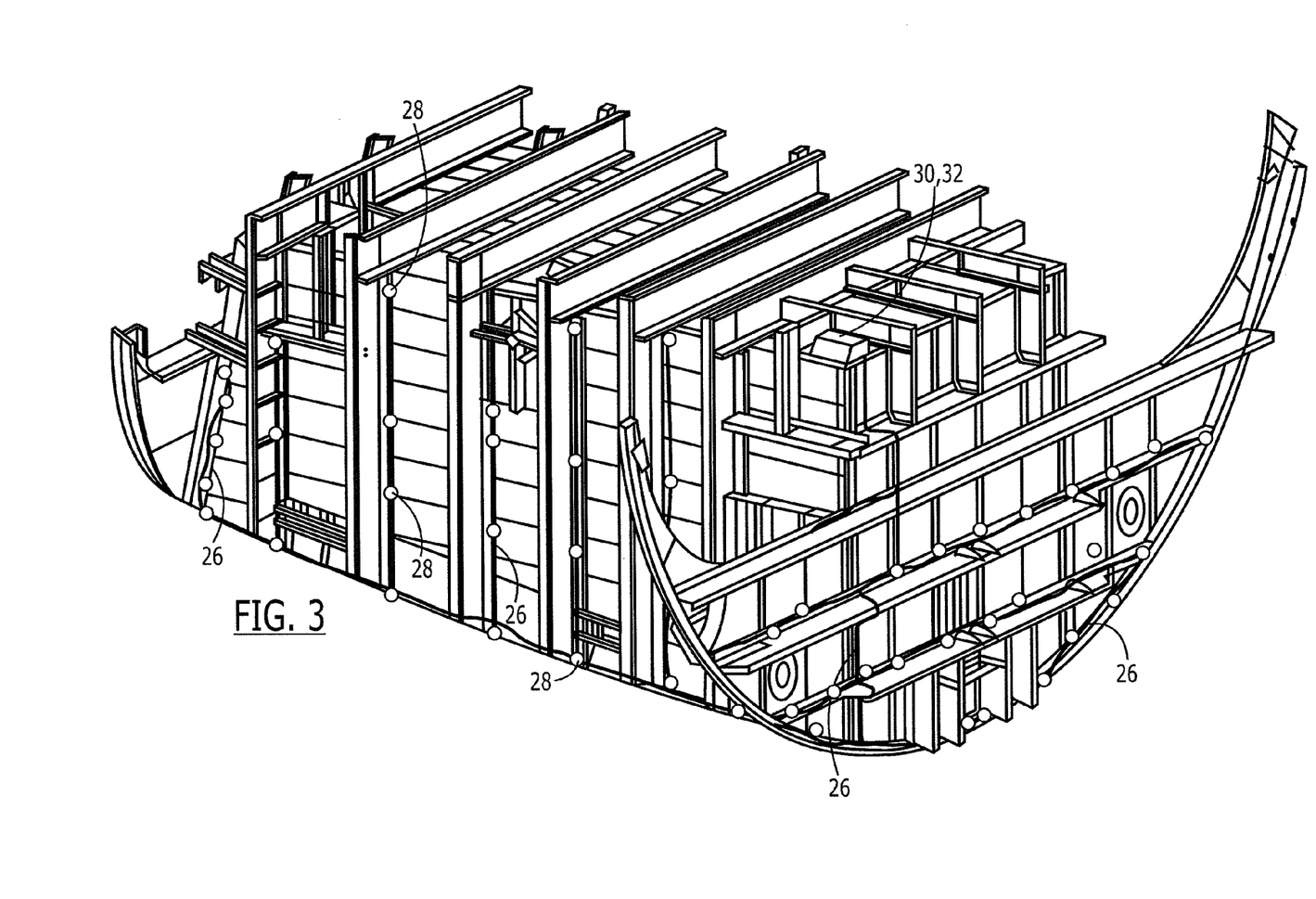
FIG. 3 is a fragmentary perspective view of an interior structural region of an aircraft and a fiber optic sensing network including a plurality of optical fibers extending along at least a portion of the interior structural region of an aircraft in accordance with one embodiment of the present invention.

As shown in FIG. 2, a structural assembly 20 is provided according to embodiments of the present invention that includes a structure 22 and a system configured to facilitate corrosion inspection of at least a portion of the structure. A variety of structures may be inspected in accordance with embodiments of the present invention. However, the system and methods of embodiments of the present invention may advantageously inspect portions of a structure that are incapable of visual inspection absent at least partial disassembly of the structure. Thus, while the system and methods of one embodiment may facilitate corrosion inspection of those portions of a structure that are in view and therefore capable of visual inspection, the system and method of one embodiment are particularly advantageous in regards to facilitating the corrosion inspection of those portions of a structure that may not be visibly inspected without at least partially disassembling the structure. For example, the structure may be an aircraft or at least a portion of the aircraft, such as an interior structural region of an aircraft as shown in FIG. 3, having one or more structural regions that are incapable of visual inspection absent at least partial disassembly of the aircraft. While an aircraft is referenced hereinbelow by way of an example of a structure to be inspected, other structures, such as other types of vehicles, buildings or the like, may be similarly inspected for corrosion, if so desired.

A system configured to facilitate corrosion inspection, such as shown in FIG. 2, may include a coating 24 disposed upon at least a portion of the structure 22. The coating may be in the form of a paint, a primer or other coating material that may be applied to at least that portion of the structure that is to be inspected in accordance with embodiments of the present invention. The coating is configured to have optical properties that change in response to corrosion. For example, the coating may change in appearance, such as by changing in color or luminescing in response to corrosion. Additionally, the change in the optical properties of the coating in response to corrosion may be visible or may only be exhibited in the non-visible spectrum. Various materials have been developed that have optical properties that change in response to corrosion and which may therefore be utilized as the coating. For example, an article by G. Liu, et al. entitled "Use of a Florescent Indicator in Monitoring Underlying Corrosion on Coated Aluminum 2024-T4," in the Journal of the Electrochemical Society, 156(4), pages C160-C166 (2009) describes a florescent indicator that is florescent under ultraviolet (UV) light in the absence of corrosion, but which becomes non-florescent in response to corrosion.

As shown in FIG. 2, the system to facilitate corrosion inspection may also include a fiber optic sensing network having an optical source 30, a plurality of optical fibers 26 and a sensor 32. The optical source may be a light source or any other source of optical signals. The optical source is configured to launch the optical signals into the plurality of optical fibers. In turn, the plurality of optical fibers are configured to expose the coating 24 to incident optical signals and to receive responsive optical signals at least partially dependent upon any change in the optical properties of the coating in response to corrosion. As shown in FIG. 3, the plurality of optical fibers may extend along and be mounted to at least a portion of the structure 22. In this regard, the plurality of optical fiber may be positioned so as to extend along at least that portion of the structure that is to be inspected for corrosion in accordance with embodiments of the present invention. As shown in FIG. 3, for example, the plurality of optical fibers may therefore extend into and/or through one or more regions of the structure that are otherwise incapable of visual inspection absent at least partial disassembly of the structure. For example, the plurality of optical fibers may extend through an interior structural region of an aircraft that may not be visually inspected without at least partially disassembling the aircraft.

Figure 4:
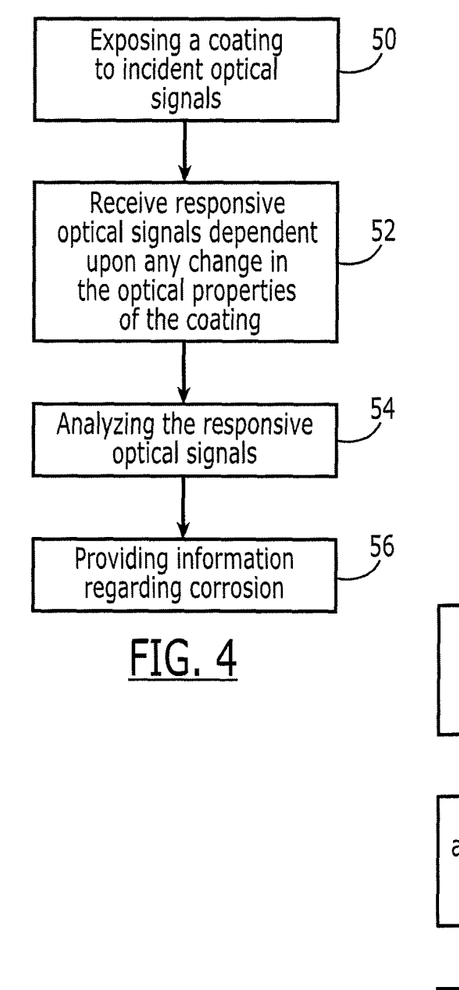
FIG. 4 is a flowchart of the operations performed in accordance with one embodiment of the present invention.

As noted above, the plurality of optical fibers 26 are configured to expose the coating 24 to incident optical signals. See, for example, operation 50 of FIG. 4. The optical fibers may therefore be configured in various manners so as to expose the coating to incident optical signals. For example, the plurality of optical fibers may include gratings 28, such as Bragg gratings, coincident with those portions of the coating to be exposed to the incident optical signals. In this regard, the plurality of optical fibers of the embodiment depicted in FIG. 3 include gratings at the circled locations such that those portions of the structure proximate the circled locations of the optical fibers are interrogated and inspected by the optical signals. The gratings may redirect at least a portion of the optical signals propagating along the optical fiber such that the redirected portion of the optical signals exit the optical fibers and expose the coating. In response to the exposure to the incident optical signals, responsive optical signals are generated with at least a portion of the responsive optical signals being introduced into the optical fiber via the grating and redirected so as to propagate along the optical fiber to the sensor 32.

In order to permit the coating 24 to be exposed to incident optical signals at a plurality of different locations, an optical fiber 26 may include gratings 28 at each of a number of locations along the optical fiber with each grating coincident with a portion of the coating that is to be exposed to incident optical signals. The gratings may be formed so as to redirect light of the same wavelength or the gratings may be formed so as to redirect light of different wavelengths such that a first grating redirects light of a first wavelength, a second grating redirects light of a second wavelength and so on. The optical source 30 may therefore introduce optical signals including each of the plurality of wavelengths that the gratings are configured to redirect. Since the gratings of this embodiment are configured to only selectively redirect light of a certain wavelength, the optical signals that are received and redirected by the gratings that are formed proximate a distal portion of the optical fiber, i.e., the portion of the optical fiber remote from or opposite from the optical source, may have a suitable intensity for interrogating the coating since the optical signals of the respective wavelength will not have already been redirected by gratings formed in an upstream portion of the optical fiber. Additionally, the wavelength dependency of the gratings permits the responsive optical signals to be distinguished and associated with a respective grating and, in turn, with the coating coincident with the respective grating as described below in order to provide more detailed information regarding corrosion at particular regions of the structure under inspection.

The sensor 32 is configured to receive the responsive optical signals from the plurality of optical fibers 26. See operation 52 of FIG. 4. In addition, the sensor one embodiment is configured to analyze a responsive optical signal in order to permit corrosion to be detected. See operation 54 of FIG. 4. Thus, the sensor may include an optical detector configured to receive and detect optical signals and an associated computing device, such as a computer or other processing device, for analyzing the responsive optical signals that are detected. The optical detector may be configured to detect the intensity of the responsive optical signals, as well as the wavelength and potentially other parameters of the responsive optical signals. The computing device may then determine whether the responsive optical signals were generated in response to the exposure of a coating 24 that has experienced corrosion or a coating that has not experienced corrosion.

In this regard, the optical properties of the coating 24 may change in response to corrosion, but may otherwise retain the same optical properties in the absence of corrosion. This change in the optical properties of the coating in response to corrosion alters the responsive optical signals that are generated in response to the exposure of the coating to incident optical signals. The computing device may therefore be configured to recognize responsive optical signals of one type to be indicative of the exposure of a coating that has not experienced corrosion and to recognize responsive optical signals of another type to be indicative of the exposure of a coating that has experienced corrosion. The responsive optical signals may differ depending upon whether the coating that has been exposed to the incident optical signals has been exposed to corrosion or not in a variety of manners depending upon the manner in which the optical properties of the coating change in response to corrosion. For example, the responsive optical signals may change in intensity, wavelength or the like in instances in which the coating that is exposed to the incident optical signals has also experienced corrosion. However, the manner in which the responsive optical signals are changed in response to the coating having experienced corrosion is generally predefined such that the computing device may readily identify responsive optical signals that are reflective of a coating that has been exposed to corrosion.

In instances in which the optical fibers 26 include a plurality of gratings 28 for redirecting light at different wavelengths, the sensor 32 may detect responsive optical signals at each of the different wavelengths. By separately analyzing the responsive optical signals at each of the different wavelengths, the computing device may separately identify whether the responsive optical signals associated with each respective grating is a product of the exposure of a coating that has experienced corrosion, or not. As such, the fiber optic sensing network of this embodiment may not only generally determine that the structure is experiencing corrosion, but may also identify which particular portions of the structure are experiencing corrosion by identifying the responsive optical signals that are indicative of the onset of corrosion to be associated with one or more respective gratings and, in turn, with those portions of the structure 22 proximate the one or more respective gratings.

In one embodiment, the coating 24 is configured to not merely have two sets of optical properties, that is, a first set of optical properties in the absence of corrosion and a second, altered set of optical properties following the onset of corrosion, but the coating may have optical properties that vary in a predefined manner over a range of appearances in response to the exposure to different levels of corrosion. As such, the coating may have a first initial set of optical properties in the absence of corrosion, a second, altered set of optical properties in response to a relatively low level of corrosion, a third altered set of optical properties in response to an intermediate level of corrosion and a fourth altered set of optical properties in response to greater levels of corrosion. Each different set of optical properties is attributable to corrosion may create different responsive optical signals in response to the exposure to incident optical signals. As such, the sensor 32 may not only detect that the responsive optical signals are indicative of the exposure of the coating to corrosion, but the sensor may detect that the responsive optical signals have been created by a coating having a respective one of the various different optical properties and, as a result, may detect the relative level of corrosion that the coating has experienced, such as a low level or corrosion, an intermediate level of corrosion or a greater level of corrosion. This additional information regarding the level of corrosion may be provided to a technician or other user and may be useful in determining the manner and the timing with which the repairs will be conducted. While a coating configured to have three different sets of optical properties in response to different levels of corrosion was provided above for purposes of example, a coating may have any number of different sets of optical properties in order to provide information regarding correspondingly different levels of corrosion with the sensor being configured to detect responsive optical signals generated by a coating having any of the various different optical properties since the relationship between the appearance of the coating, the level of corrosion and the characteristics of the responsive optical signals generated by exposure of the coating to the incident optical signals may be predefined.

Following the analysis of the responsive optical signals, the results of the analysis may be provided to a technician or other user in various manners. See operation 56 of FIG. 4. For example, the system may include a user interface 34, such as a display, for providing information regarding any corrosion of the structure 22 that is detected in response to analysis of the responsive optical signals. In this regard, the display may be driven by the computing device to provide information not only alerting the technician that corrosion may be occurring, but also providing information, in some embodiments, regarding the location at which the corrosion may be occurring. In instances in which the structure to be inspected is an aircraft, the display or other user interface associated with the fiber optic sensing network may be a unique display dedicated to the inspection process or an existing display or other user interface of the aircraft. In addition or alternatively, the results of the analysis of the responsive optical signals including information regarding the detection of corrosion and, in some embodiments, the location, if any, at which corrosion has occurred may also be stored for subsequent review and/or analysis.

In instances in which corrosion is detected, appropriate remedial efforts may commence. In this regard, the structure 22 may be at least partially disassembled and that portion of the structure that is experiencing corrosion may be repaired, replaced or steps taken to otherwise mitigate the deleterious affects of corrosion. In the embodiment described above in which the responsive optical signals not only provide information regarding the onset of corrosion, but also provide information regarding the location at which the corrosion is occurring, the at least partial disassembly of the structure may be selectively performed so as to only disassemble those portions of the structure that are experiencing corrosion and not other portions of the structure that are not experiencing corrosion, thereby permitting the repairs to be conducted in a more efficient and cost effective manner. In addition, by permitting the inspection of the structure including those portions of the structure that are not otherwise available for visual inspection without at least partial disassembly of the structure, the structure may be inspected on a more regular basis and without taking the structure out of service. As such, corrosion may be detected, on average, sooner following the onset of the corrosion such that repairs may be undertaken prior to the corrosion having an opportunity to cause as much damage to the structure as may have occurred in other instances in which inspections occur less frequently, such as every few years, as a result of the necessity to at least partially disassemble the structure in order to conduct the inspection.

In instances in which corrosion is not detected, however, the inspection process including the exposure of the coating to incident optical signals, the reception of the responsive optical signal and the analysis of the responsive optical signals to detect corrosion may be repeated, such as in accordance with a predefined schedule.

Figure 5:
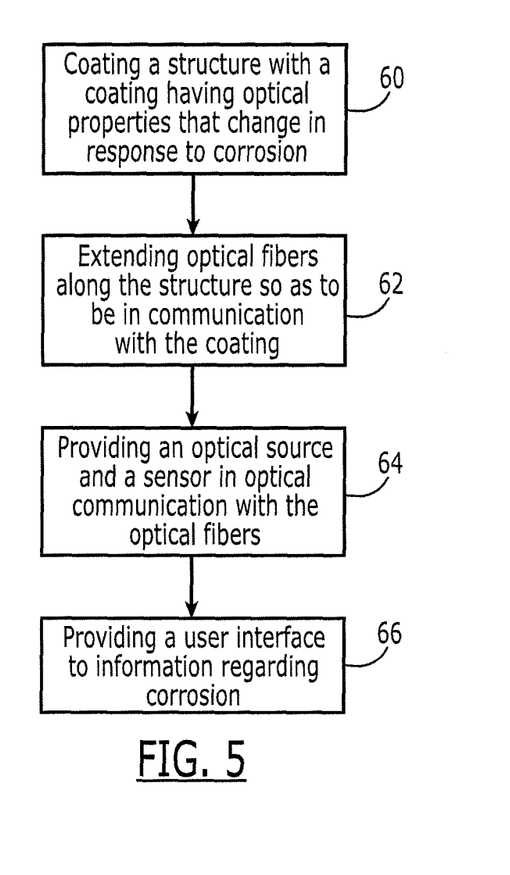
FIG. 5 is a flowchart of the operations performed in accordance with another embodiment of the present invention.

As shown in FIG. 3 and discussed above, the corrosion inspection system is an integrated portion of the structural assembly 20. In accordance with another embodiment, therefore, a method is provided for constructing a corrosion inspection system. As shown in FIG. 5 and, in particular, in operation 60 of FIG. 5, the method of this embodiment coats at least a portion of a structure with a coating having optical properties that change in response to corrosion. As described above, for example, at least a portion of the structure may be coated with a coating that is configured to change in color or to luminesce in response to corrosion. The method of this embodiment also extends a plurality of optical fibers along at least the portion of the structure that is coated such that the optical fibers are in optical communication with the coating, as shown in operation 62. As also described above, the optical fibers may be extended along a region of the structure that is incapable of visual inspection absent at least partial disassembly of the structure, such as within an interior structural region of an aircraft as shown in FIG. 3. For example, the optical fibers may be extended along and attached to ribs or other structural members that are desired to be inspected for corrosion. Further, the method of this embodiment provides an optical source configured to provide incident optical signals to the plurality of optical fibers and a sensor configured to receive responsive optical signals from the plurality of optical fibers following interaction of the optical signals with the coating so as to permit the responsive optical signals to be analyzed to detect corrosion. See operation 64 of FIG. 5. As shown in operation 66, the method may also provide a user interface configured to provide information regarding corrosion of the structure in response to analysis of the responsive optical signals by the sensor.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A structural assembly configured to facilitate corrosion inspection, the structural assembly comprising:
    a structure;
    a paint or primer applied to at least a portion of a surface of the structure and configured to have optical properties that change in response to corrosion; and
    a fiber optic sensing network comprising a plurality of optical fibers configured to expose the paint or primer to incident optical signals and to receive responsive optical signals at least partially dependent upon any change in the optical properties of the paint or primer in response to corrosion, the fiber optic sensing network also comprising a sensor configured to receive the responsive optical signals from the plurality of optical fibers,
    wherein the paint or primer applied to at least a portion of the surface of the structure is physically distinct from the plurality of optical fibers.

2. A structural assembly according to claim 1 wherein the paint or primer is configured to change in color or to luminesce in response to corrosion.

3. A structural assembly according to claim 1 wherein the plurality of optical fibers each extend along at least a portion of the structure and emit incident optical signals from a location along the optical fiber that is spaced apart from the paint or primer.

4. A structural assembly according to claim 3 wherein the plurality of optical fibers comprise a plurality of gratings configured to redirect light having different respective wavelengths to different portions of the structure, and wherein the sensor is further configured to analyze the responsive optical signals and to detect corrosion from a respective portion of the structure.

5. A structural assembly according to claim 1 further comprising a user interface configured to provide information regarding corrosion of the structure in response to analysis of the responsive optical signals by the sensor.

6. A structural assembly according to claim 1 wherein at least a portion of the structure inspected by the fiber optic sensing network comprises a region that is incapable of visual inspection absent at least partial disassembly of the structure.

7. A structural assembly according to claim 6 wherein at least the portion of the structure inspected by the fiber optic sensing network comprises an interior structural region of an aircraft.

8. A method of constructing a corrosion inspection system, the system comprising:
    applying a paint or primer to at least a portion of a surface of a structure with the paint or primer having optical properties that change in response to corrosion;
    extending a plurality of optical fibers along at least the portion of the structure that is coated such that the optical fibers are in optical communication with the paint or primer, wherein the paint or primer is applied to at least a portion of the surface of the structure so as to be physically distinct from the plurality of optical fibers; and
    providing an optical source configured to provide incident optical signals to the plurality of optical fibers and a sensor configured to receive responsive optical signals from the plurality of optical fibers following interaction of the optical signals with the paint or primer so as to permit the responsive optical signals to be analyzed to detect corrosion.

9. A system according to claim 8 wherein the paint or primer is configured to change in color or to luminesce in response to corrosion.

10. A method according to claim 8 wherein extending the optical fibers comprises extending the optical fibers along a region of the structure that is incapable of visual inspection absent at least partial disassembly of the structure.

11. A method according to claim 10 wherein extending the optical fibers further comprises extending the optical fibers within an interior structural region of an aircraft.

12. A method according to claim 8 wherein extending the optical fibers comprises extending each optical fiber along at least the portion of the structure so as to emit incident optical signals from a location along the optical fiber that is spaced apart from the paint or primer.

13. A method of inspecting a structure for corrosion, the method comprising:
    exposing a paint or primer applied to at least a portion of a surface of the structure to incident optical signals being delivered by at least one optical fiber, the paint or primer being configured to have optical properties that change in response to corrosion, wherein the paint or primer applied to at least a portion of the surface of the structure is physically distinct from the at least one optical fiber;
    receiving responsive optical signals via at least one optical fiber in response to having exposed the paint or primer to the incident optical signals with the responsive optical signals being at least partially dependent upon any change in the optical properties of the paint or primer in response to corrosion; and
    analyzing the responsive optical signals to detect corrosion.

14. A method according to claim 13 wherein the paint or primer is configured to change in color or to luminesce in response to corrosion.

15. A method according to claim 13 further comprising delivering the incident optical signals and returning the responsive optical signals via a plurality of optical fibers each extending along at least a portion of the structure, wherein delivering the incident optical signals comprises delivering the incident optical signals from a location along the optical fiber that is spaced apart from the paint or primer.

16. A method according to claim 13 wherein analyzing the responsive optical signals to detect corrosion comprises detecting responsive optical signals that result from having exposed the paint or primer to incident optical signals following the change in the optical properties of the paint or primer in response to corrosion.

17. A method according to claim 15 wherein delivering the optical signals comprise delivering the optical signals via a plurality of gratings defined by the plurality of optical fibers with the gratings configured to redirect light having different respective wavelengths to different portions of the structure, and wherein analyzing the responsive optical signals comprises analyzing the optical signals returning from the different portions of the structure and detecting corrosion from a respective portion of the structure.

18. A method according to claim 13 wherein exposing the paint or primer comprises exposing the paint or primer disposed upon at least a portion of the structure that is incapable of visual inspection absent at least partial disassembly of the structure.

19. A method according to claim 18 wherein exposing the paint or primer further comprises exposing the paint or primer disposed upon an interior structural region of an aircraft.

20. A method according to claim 13 wherein exposing the paint or primer, receiving responsive optical signals and analyzing the responsive optical signals are repeated in accordance with a predefined schedule.

* * * * *